United States Patent
Rogers

(10) Patent No.: US 6,310,197 B1
(45) Date of Patent: Oct. 30, 2001

(54) TRANSLATION ENHANCER ELEMENT OF THE HUMAN AMYLOID PRECURSOR PROTEIN GENE

(75) Inventor: Jack Rogers, Jamaica Plain, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/188,118

(22) Filed: Nov. 9, 1998

Related U.S. Application Data

(60) Provisional application No. 60/065,175, filed on Nov. 12, 1997.

(51) Int. Cl.$^7$ .......................... C07H 21/04; C12N 15/09; C12N 5/10; C12N 15/03
(52) U.S. Cl. .................. 536/24.1; 435/320.1; 435/69.1; 435/325; 435/252.3; 435/89
(58) Field of Search .................................. 536/231, 24.1, 536/24.3; 435/320.1, 69.1, 325, 252.3, 89

(56) References Cited

U.S. PATENT DOCUMENTS 5,218,100  6/1993  Muller-Hill et al. ................ 536/23.5

FOREIGN PATENT DOCUMENTS 276 723  1/1987  (EP) .............................. C07H/21/04

OTHER PUBLICATIONS

Lahiri, "Molecular Analysis of the Promoter Region of the Gene Encoding the Beta–Amyloid Precursor Protein," *Indian J. Biochem. Biophys.* 32:329–355 (1995).

Del Bo, et al., "Reciprocal Control of Inflammatory Cytokines, IL–1 and IL–6, and β–Amyloid Production in Cultures," *Neurosci. Letters* 188:70–74 (1995).

Goldgaber et al, PNAS, 86:7606–9, Oct. 1989.*

Abraham, et al., "Immunochemical Identification of the Serine Protease Inhibitor $\alpha_1$–Antichymotrypsin in the Brain Amyloid Deposits of Alzheimer's Disease," *Cell* 52:487–501 (1988).

Busciglio, et al., "Generation of βGeneration of β–Amyloid in the Secretory Pathway in Neuronal and Nonneuronal Cells," *Proc. Natl. Acad. Sci. USA* 90:2092–2096 (1993).

Corder, et al., "Gene Dose of Apolipoprotein E Type 4 Allele and the Risk of Alzheimer's Disease in Late Onset Families," *Science* 261:921–923 (1993).

Das, et al., "Expression of the Alzheimer Amyloid–Promoting Factor Antichymotrypsin Is Induced in Human Astrocytes by IL–1," *Neuron* 14:447–456 (1995).

Goate, et al., "Segregation of a Missense Mutation in the Amyloid Precursor Protein Gene with Familial Alzheimer's Disease," *Nature* 349:704–706 (1991).

Hentze, et al., "Molecular Control of Vertebrate Iron Metabolism: mRNA–Based Regulatory Circuits Operated by Iron, Nitric Oxide, and Oxidative Stress," *Proc. Natl. Acad. Sci. USA* 93:8175–8182 (1996).

Ho, et al., "The Alternatively Spliced Kunitz protease Inhibitor Domain Alters Amyloid β Protein Precursor Processing and Amyloid β Protein Production in Cultured Cells," *J. Biol. Chem.* 271:30929–30934 (1996).

Kang, et al., "The Precursor of Alzheimer's Disease Amyloid A4 Protein Resembles a Cell–Surface Receptor," *Nature* 325:733–736 (1987).

LeBlanc, et al., "Differential APP Gene Expression in Rat Cerebral Cortex, Meninges, and Primary Astroglial, Microglial and Neuronal Cultures," *FEBS Letters* 292:171–178 (1991).

Leedman, et al., "Thyroid Hormone Modulates the Interaction Between Iron Regulatory Proteins and the Ferritin mRNA Iron–Responsive Element," *J. Biol. Chem.* 271:12017–12023 (1996).

Ma, et al., "Amyloid–Associated Proteins $\alpha_1$–Antichymotrypsin and Apolipoprotein E Promote Assembly of Alzheimer β–Protein into Filaments," *Nature* 372:92–94 (1994).

Neve, et al., "A Comprehensive Study of the Spatiotemporal Pattern of β–Amyloid Precursor Protein mRNA and Protein in the Rat Brain: Lack of Modulation by Exogenously Applied Nerve Growth Factor," *Molec. Brain Res.* 39:185–197 (1996).

Nieto–Sampedro, et al., "Interleukin–1–Like Activity in Rat Brain: Sources, Targets, and Effect of Injury," *J. Neurosci. Res.* 17:214–219 (1987).

Pantopoulos, et al., "Rapid Responses to Oxidative Stress Mediated by Iron Regulatory Protein," *EMBO J.* 14:2917–2924 (1995).

Quon, et al., "Formation of β–Amyloid Protein Deposits in Brains of Transgenic Mice," *Nature* 352:239–241 (1991).

Rogers, "Ferritin Translation by Interleukin–1 and Interleukin–6: The Role of Sequences Upstream of the Start Codons of the Heavy and Light Subunit Genes," *Blood* 87:2525–2537 (1996).

Rogers, et al., "Translational Enhancement of H–Ferritin mRNA by Interleukin–1β Acts Through 5' Leader Sequences Distinct from the Iron Responsive Element," *Nucleic Acids Res.* 22:2678–2686 (1994).

(List continued on next page.)

*Primary Examiner*—Gary L. Kunz
*Assistant Examiner*—Sharon L Turner
(74) *Attorney, Agent, or Firm*—Michael A. Sanzo; Pillsbury Winthrop LLP

(57) ABSTRACT

The present invention is directed to a DNA element that enhances the translation of the human amyloid precursor protein (APP) gene. The enhancer may be incorporated into expression vectors to enhance recombinant protein production. In addition, the invention is directed to an assay that utilizes vectors containing the translation enhancer element for the purpose of identifying agents that modulate the expression of the human amyloid precursor protein. These agents will ultimately be used to suppress APP expression in patients with Alzheimer's disease.

10 Claims, No Drawings

OTHER PUBLICATIONS

Rogers, et al., "Translational Control During the Acute Phase Response," *J. Biol. Chem.* 265:14572–14578 (1990).

Sauvage, et al., "Alternative Polyadenylation of the Amyloid Protein Precursor mRNA Regulates Translation," *EMBO J.* 11:3099–3103 (1992).

Selkoe, "Amyloid β–Protein and the Genetics of Alzheimer's Disease," *J. Biol. Chem.* 271:18295–18298 (1996).

Scheuner, et al., "Secreted Amyloid β–Protein Similar to That in the Senile Plaques of Alzheimer's Disease Is Increased In Vivo by the Presenilin 1 and 2 APP Mutations Linked to Familial Alzheimer's Disease," *Nature Med.* 2:864–870 (1996).

Sheng, et al., "In Vivo and In Vitro Evidence Supporting a Role for the Inflammatory Cytokine Interleukin–1 as a Driving Force in Alzheimer's Pathogenesis," *Neurobiol. Aging* 17:761–766 (1996).

Van Nostrand, et al., "The Predominant Form of the Amyloid β–Protein Precursor in Human Brain is Protease Nexin 2," *Proc. Natl. Acad. Sci. USA* 88:10302–10306 (1991).

* cited by examiner

TRANSLATION ENHANCER ELEMENT OF THE HUMAN AMYLOID PRECURSOR PROTEIN GENE

CROSS REFERENCE TO RELATED APPLICATIONS

The present application claims priority to U.S. Provisional application No. 60/065,175, filed on Nov. 12, 1997 (now abandoned).

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is directed to a nucleic acid element that enhances the translation of the human amyloid precursor protein (APP) gene. This element may be ligated to other structural genes to enhance recombinant protein production. In addition, it may be ligated to reporter gene sequences and used in assays for the purpose of identifying factors that alter the expression of APP. In addition the sequence can be used as a therapeutic target for down regulating APP production.

BACKGROUND OF THE INVENTION

Alzheimer's disease develops as the result of a complex series of steps that ultimately lead to neuronal cell death and the loss of cognitive function. At present, two steps appear to be of particular importance. The first is a synthesis of the amyloid precursor protein (APP) and its processing into the Aβ peptides, which then polymerize and deposit as the amyloid filaments that are the hallmark of Alzheimer's disease (Selkoe, *J. Biol. Chem.* 271:18295 (1996); Scheuner, et al., *Nature Med.* 2:864 (1996); Goate, et al., *Nature* 349:704 (199 1)). Coupled to this process is a special form of inflammation and acute phase response in the brain that leads to an increase in the production of amyloid-associated proteins, $\alpha_1$-antichymotrypsin (ACT) and complement activation (Abraham, et al., *Cell* 52:487 (1989)). In vitro studies have shown that ACT and another amyloid-associated protein, apolipoprotein-E (ApoE), regulate the polymerization of Aβ peptides into amyloid filaments (Yee, et al., *Nature* 372:92 (1994)). The ApoE 4 and, possibly, the ACT-A alleles are inherited risk factors for Alzheimer's disease (Corder, et al., *Science* 261:921 (1992)).

Several facts suggest a direct connection between increased APP levels and the development of Alzheimer's disease and further suggest that such an increase may be linked to inflammatory mechanisms:

a) Down syndrome brains in trisomy-16 mice show increased APP protein levels beyond the 0.5-fold increase that would be expected by gene dosage (Neve, et al., *Mol. Brain Res.* 39:185 (1996)).

b) Over-expression of APP protein in transgenic mice is necessary, even in the presence of FAD mutations, for sufficient Aβ peptide production to lead to the development of amyloid filament deposits and an Alzheimer's-like pathology (Quon, et al., *Nature* 352:239 (1991)). Furthermore, APP protein synthesis correlates with AP peptide production both in vitro and in vivo (Ho, et al., *J. Biol. Chem.* 271:30929 (1996)).

c) Traumatic brain injury, a known risk factor for Alzheimer's disease, increases IL-1 as well as APP-immunoreactivity in rat brain (Nieto-Sampedro, et al., *J. Neurosci. Res.* 17:214 (1987)).

d) IL-1 injected into the rat cerebral cortex increases the steady-state levels of APP protein at the site of the lesion (Sheng, et al., *Neurobiol. Aging* 17:761 (1996)) and primary astrocytes have been shown to be a source of secreted Aβ peptides (Buscigio, et al., *Proc. Natl. Acad. Sci. U.S.A.* 90:2092 (1993)).

The identification of the mechanisms by which inflammation leads to the overproduction of APP in brain cells may lead to new therapies for controlling Alzheimer's disease. Beyond this, the discovery of new methods and elements for regulating gene expression will provide new opportunities for controlling the production of recombinant genes both in vitro and in vivo.

SUMMARY OF THE INVENTION

The present invention is based upon the discovery of a distinct DNA element that increases the rate at which the mRNA transcribed from the amyloid precursor protein (APP) gene is translated. This element may be combined with other genes to increase recombinant protein production without increasing transcriptional activity.

In its first aspect, the invention is directed to a substantially pure DNA molecule comprising the translation enhancer element of APP operably linked to a non-homologous gene, i.e., a gene other than that encoding human APP. The translation enhancer element consists essentially of the nucleotide sequence of SEQ ID NO:1 and, in a preferred embodiment, the nonhomologous gene is located at a site between 10 and 100 nucleotides 3' to the last 3' nucleotide in the enhancer.

In another aspect, the present invention is directed to a vector for recombinantly expressing a peptide or protein in a eukaryotic cell. The vector contains a promoter active in the cell; a translation enhancer element having a sequence consisting essentially of that of SEQ ID NO:1 lying 3' to the promoter; and 5' to a DNA sequence encoding the peptide or protein for recombinant production. The sequence encoding the peptide or protein should be located 3' to the enhancer element; be operably linked to the promoter; and be non-homologous with respect to the translation enhancer element. In a preferred embodiment, the gene undergoing recombinant expression is located at a site between 10 and 100 nucleotides 3' to the last 3' nucleotide in the enhancer. These vectors may be used to transform a variety of host cells, preferably eukaryotic host cells, using standard techniques for transformation. Cells transformed in this manner are also within the scope of the present invention.

The invention is also directed to a method for recombinantly producing protein in which host cells transformed with the vector discussed above are grown, in vitro or in vivo, and recombinant protein is then purified either from the host cells or from the growth medium surrounding the cells. Purification may be accomplished by standard biochemical techniques including precipitations, chromatography on various matrices, electrophoretic techniques, affinity chromatography, etc. Optionally, the method may include exposing host cells to an inducer, e.g. a cytokine such as interleukin-1α and interleukin-1β, that increases the activity of the translation enhancer element. An optimal concentration of inducer can be determined by titrating it into the system and measuring the amount of recombinant protein produced at each concentration. In addition to being directed to such methods, the invention includes the recombinant peptides or proteins that are produced by these methods.

In another aspect, the present invention is directed to a method for assaying test compounds for their ability to alter the expression of human APP. This may be accomplished by preparing a vector containing a promoter, the translation enhancer element, and a non-homologous gene operably linked to the element. Preferably, the non-homologous gene will produce a product that can be quantitated with relative ease, e.g., the chloramphenicol acetyltransferase gene may be used for this purpose. Gene expression is then measured in the presence and absence of the test compound in order to determine whether there is either an enhancement or inhibition of expression. Assays may be carried out either using in vitro systems or after transforming host cells with the vector. Because over-expression of APP has been associated with Alzheimer's disease, agents that inhibit the activity of the translation enhancer element are of particular interest. Thus, the present invention includes methods in which the test compounds used are antisense agents specifically directed to the translation enhancer element. These antisense compounds should be nucleic acids complementary to a region of SEQ ID NO:1 that is at least ten bases in length. Agents of this type may undergo a variety of modifications to increase their effectiveness. Other test compounds that can be used in the assays include RNA targeting compounds that alter the enhancer function of the sequence. Such compounds may act by recognizing portions of the secondary structure assumed by different RNAs. In addition pharmacological reagents and inhibitory receptor-mediated ligands may be tested.

DEFINITIONS

The invention description provided herein uses a number of terms that refer to recombinant DNA technology. In order to provide a clear and consistent understanding of the specification and claims, including the scope to be given such terms, the following definitions are provided.

Substantially pure: As used herein, the term "substantially pure" refers to a biological component, protein or nucleic acid, that has been separated from other accompanying biological components so that, typically, it comprises at least 85 percent of a sample, with greater percentages being preferred. Many means are available for assessing the purity of nucleic acids and proteins within a sample, including analysis by polyacrylamide gel electrophoresis, chromatography and analytical centrifugation.

Operably linked: The term "operably linked" refers to genetic elements that are joined in a manner that enables them to carry out their normal functions. For example, a gene is operably linked to a promoter when its transcription is under the control of the promoter and the transcript produced is correctly translated into the protein normally encoded by the gene.

Consists essentially of: The term "consists essentially of," or "consisting essentially of," is used in conjunction with the sequence of the translation enhancer element. It indicates that the translation enhancer encompasses sequences exactly the same as that shown in SEQ ID NO:1, as well as DNA elements with differences that are not substantial, as evidenced by their retaining the basic, qualitative functional properties of the element. In particular, it is anticipated that minor substitutions, additions or deletions of nucleotides may take place within the sequence at positions that do not affect its ability to enhance the translation of an operably linked gene.

Non-homologous: The term "non-homologous" is used herein to indicate that the APP translation enhancer element is joined to a gene other than the one it would normally be joined to in nature, i.e., the translation enhancer element is joined to something other than the human APP gene.

Promoter: A promoter is the DNA sequence at which transcription is initiated. If the promoter is of the inducible type, then its activity increases in response to an inducing agent.

Complementary Nucleotide Sequence: The term "complementary nucleotide sequence," refers to a sequence that would arise by normal base pairing. For example, the nucleotide sequence 5'-AGA-3' would have the complementary sequence 5'-TCT-3'.

Expression: Expression is the process by which a polypeptide is produced from DNA. The process involves the transcription of the gene into mrNA and the subsequent translation of the mRNA into a polypeptide.

Host: Any prokaryotic or eukaryotic cell that is the recipient of a replicable expression vector or cloning vector is the "host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g., Sambrook et al., Molecular Cloning: A Laboratory Manual, 2nd ed. Cold Spring Harbor (1989)).

Cloning vector: A cloning vector is a DNA sequence (typically a plasmid or phage) which is able to replicate autonomously in a host cell, and which is characterized by one or a small number of restriction endonuclease recognition sites. A foreign DNA fragment may be spliced into the vector at these sites in order to bring about the replication and cloning of the fragment. The vector may contain one or more markers suitable for use in the identification of transformed cells. For example, markers may provide tetracycline or ampicillin resistance.

Expression vector: An expression vector is similar to a cloning vector but is capable of inducing the expression of the DNA that has been cloned into it, after transformation into a host. The cloned DNA is usually placed under the control of (i.e., operably linked to) certain regulatory sequences such as promoters or enhancers. Promoter sequences may be constitutive, inducible or repressible.

Gene. As used herein, the term "gene" refers to a nucleic acid sequence containing a template for a nucleic acid polymerase, in eukaryotes, RNA polymerase II. Genes are transcribed into mRNAs that are then translated into protein.

DETAILED DESCRIPTION OF THE INVENTION

The present invention is directed to a translation enhancer element that was first identified in the 5' untranslated region (5' UTR) of the human amyloid precursor protein gene. The element is defined by its structure as shown in SEQ ID NO:1. However, it will be understood that the invention encompasses not only sequences identical to that shown, but also sequences that are essentially the same as evidenced by their retaining the basic functional characteristic of enhancing the translation of an operably linked structural gene. In addition, the present invention encompasses methods of recombinantly producing protein which utilize this element and methods for assaying compounds for their ability to inhibit APP expression.

I. APP Translation Enhancer Element

The APP translation enhancer element is 90 nucleotides in length and may be obtained by a wide variety of methods. One method that has proven to be effective is to isolate the element from the 5' untranslated region of a human APP clone, obtained by screening the cDNA library of a cell type known to produce large amounts of APP. For example, the procedure of Kang, et al. (*Nature* 325:733 (1987)) can be used to clone the APP cDNA by expression screening a library of fetal brain cDNAs. Other cells that may be utilized include human astrocytoma cells and human astrocytes.

Once the complete APP cDNA has been isolated, the translation enhancer element may be obtained by digesting clones with appropriate restriction enzymes and subcloning fragments containing the element. In the case of the library discussed above, the CD plasmids containing the cloned APP cDNA can be digested with a combination of SmaI and HindIII to obtain a 3 kB fragment. This may then be incorporated into either a cloning vector or an expression vector. For example, the SmaI/HindIII digestion product may be inserted into compatible StuI/HindIII sites in the 5' UTR of pSV$_2$CAT. The 3 kB APP gene body may then be cut out of this clone (designated pSV$_2$(APP-1)CAT) by digestion with NruI and HindIII to leave behind the APP gene 5' UTR fused to the CAT reporter gene.

The plasmid produced in this manner may be transfected into host cells using standard techniques (i.e., calcium phosphate precipitation, liposome transfer, electroporation, etc.) and the host cells grown to produce large amounts of plasmid. Alternatively, host cells may be used in the assays described in section III below. When cells, e.g. astrocytoma cells, are transfected with pSV$_2$(APP)CAT, they produce a chimeric transcript in which 90 nucleotides of the APP gene 5' UTR are part of a 117 nucleotide 5' leader sequence.

Although the above procedure is suitable for obtaining the human APP translation enhancer, many alternative techniques have been described for isolating genetic elements and it is expected that these can be adapted to the isolation of the APP translation enhancer with relatively little effort (see e.g., Sambrook, et al., *Molecular Cloning: A Laboratory Manual*, 2nd ed., Cold Spring Harbor Press (1989)). Thus, the enhancer element my be chemically synthesized or cDNA libraries may be screened using labeled PCR-generated probes corresponding to regions of the known APP gene sequence. In general, such probes should be at least 14 nucleotides long and should not be selected from a region known to be conserved among proteins. In one especially preferred alternative, the APP gene sequence may be used to construct PCR primers for the purpose of amplifying the enhancer element.

II. Method of Recombinantly Producing Protein

One of the main uses for the human APP translation enhancer element is in the recombinant production of protein. To make an appropriate expression vector, the techniques discussed above can be used to obtain the enhancer element which should then be positioned downstream from the start site of transcription and upstream from the structural gene segment undergoing expression. The exact position relative to the promoter and gene cap site is not critical to the invention but, preferably, the cap site will be between 10 and 100 nucleotides 3' to the last 3' nucleotide in the enhancer. In all cases, the enhancer should be between the AUG codon and the transcription promoter. Other elements present will vary depending upon host cell type, but will generally include sequences involved with the initiation of transcription and translation and sequences signaling the termination of transcription Transcriptional enhancer sequences may also be present. Examples of eukaryotic promoters that may be used include the promoter of the mouse metallothionein I gene (Haymer, et al., *J. Mol. Appl. Gen.* 1:273 (1982)); and TK promoter of Herpes virus (McKnight, *Cell* 31:355–365 (1982)); the SV40 early promoter (Benoist, et al., *Nature* 290:304 (1981)), etc.

It is widely known that translation of eukaryotic mRNA is initiated at the codon which encodes the first methionine of a gene. For this reason, the linkage between a promoter and the DNA structural sequence should not contain any intervening codons for methionine. The presence of such codons results either in the formation of a fusion protein (if the AUG codon is in the same reading frame as the structural sequence) or a frame-shift mutation (if the AUG codon is not in the same reading frame). The insertion of the enhancer should not, in itself, generate any misplaced start codons A large number of plasmids suitable for use in eukaryotes have been described (Botstein, et al., *Miami Winter Symp.* 19:265 (1982); Broach, *Cell* 28:203 (1982); Bollon, et al., *J. Cin. Hematol. Oncol.* 10:39 (1980); Maniatis, in *Cell Biology: A Comprehensive Treatise*, vol. 3, Academic Press, M.Y. pp. 563–608 (1980)). In addition, the translation enhancer element may be incorporated into DNA constructs designed for homologous recombination (see Capecchi, TIG 5:70 (1989); Mansour, et al., *Nature* 336:348 (1988); Thomas, et al., *Cell* 51:503 (1987); and Doetschman, et al., *Nature* 330:576 (1987)).

Once the vector or DNA sequence has been prepared, it may be introduced into an appropriate host cell by any suitable means of transfection (e.g., calcium phosphate and lipofectin precipitation). Large amounts of recipient cells may then be grown in a medium which selects for vector-containing cells. If desired, an inducer may be introduced into the growth medium for the purpose of increasing the activity of the translational enhancer element. Inducers that have been found to be effective in this regard are interleukinin-1α and interleukin-1β but it is possible that other cytokines may be used as well.

The expressed recombinant protein may be purified in accordance with conventional methods such as extraction, precipitation, chromatography, affinity chromatography, electrophoresis and the like. The exact procedure used will depend upon both the specific protein produced and the specific expression system utilized.

III. Assay for Compounds Modulating APP Expression

Overproduction of the APP protein has been closely associated with the development of Alzheimer's disease. Therefore, assays for the identification of compounds that either inhibit or enhance expression are of considerable interest. Compounds that inhibit expression have potential use as therapeutic agents whereas compounds enhancing expression would have use in scientific studies examining the pathogenesis of Alzheimer's disease.

Assays may be performed using an expression vector in which the APP translation enhancer is located upstream from a reporter gene. For example, the pSV$_2$(APP)CAT plasmids described in section I may be utilized. These plasmids should be transfected into appropriate host cells, e.g., astrocytes or astrocytoma cells, which are then divided equally into sample wells and exposed to test compounds. The effect of the test compounds on reporter gene expression can then be determined by comparing the expression seen in the presence of test compound with that taking place in its absence.

In order to confirm that compounds are acting at the level of translation, the mRNA content of exposed and unexposed cells may be compared (see Examples section for a description of one procedure that can be used for this purpose). If desired, assays may be carried out in the presence of cytokines such as interleukin-1α or interleukin-1β to determine whether test compounds alter the enhancement of translational activity typically seen with these compounds.

One group of test compounds that are of particular interest are oligonucleotides complementary to segments of the translation enhancer sequence. These oligonucleotides should be complementary to at least 10 bases within the enhancer element and, preferably, 15 bases or more. Oligonucleotides which are found to alter translational activity may be derivatized or conjugated in order to increase their effectiveness. For example, nucleoside phosphorothioates may be substituted for their natural counterparts (see Cohen, *Oligodeoxynucleotides, Antisense, Inhibitors of Gene Expression*, CRC Press (1989)). The oligonucleotides may also be designed for delivery in vivo for the purpose of inhibiting APP expression. When this is done, it is preferred that the oligonucleotide be administered in a form that enhances uptake by cells. For example, the oligonucleotide may be delivered by means of a liposome, retrovirus, or conjugated to a peptide that is ingested by cells (see, e.g., U.S. Pat. Nos. 4,897,355 and 4,394,448). Other methods for enhancing the efficiency of oligonucleotide delivery are well-known in the art and are also compatible with the present invention.

RNA targeting compounds, pharmacological reagents and inhibitory receptor-mediated ligands may also be tested in the assays. The most preferred of these are RNA targeting compounds that act by recognizing the secondary structure that results from the folding of RNA.

EXAMPLES

I. Methods

Preparation of Primary Human Astrocytes

Primary human astrocytes were prepared by trypsinization of human fetal brain tissue by a previously described method (Das, et al., *Neuron* 14; 447 (1995)). Cells were seeded onto poly-L-lysine (10 μg/ml) coated plates and were grown to 70% confluence in DMEM medium, (low glucose) supplemented with 10% fetal bovine serum. In order to eliminate microglia, the cultures were treated with 5 mM H-Leu-O-methylester (Guilian, *J. Neurosci. Res.* 18:155 (1987)). For immunofluorescence, cells were replated at a density of 100,000 cells per 60-mm petri dish on poly-L-lysine coated glass coverslips and grown for 24 hours in 0.5 ml of medium to allow the cells to attach. The presence of glial fibrillary acidic protein (GFAP) was detected by immunofluorescent staining of formaldehyde fixed cells using a 1:10 dilution of rabbit IgG$_1$, antibody specific for human GFAP. Primary GFAP-specific antibody was added to the coverslips for 30 minutes at room temperature in phosphate buffered saline and 10% goat serum. The secondary antibodies used were goat anti-rabbit IgG conjugated to fluorescein isothiocyanate at a dilution of 1:100 (Boehringer). Fluorescence microscopy scored the cells used in the metabolic experiments as 95% pure astrocytes. Antibodies to neuronal specific microtubule associated protein (MAP-2) and beta-3-tubulin failed to label the astrocyte cultures. The U373MG astrocytoma cell line was cultured on 100 mm uncoated dishes to 60–80% confluence in DMEM medium supplemented with 10% fetal bovine serum.

Determination of APP Protein Synthesis

Intracellular APP protein synthesis was determined in primary astrocytes after plating cells in equal numbers into 8 microtiter wells prior to each treatment (1×10$^5$ cells per well in 96 well dishes). Astrocytes in 5 rows of 12 wells were stimulated for 16 hours with: (1) 0.5 mg/ml recombinant IL-1α; (2) 0.5 mg/ml recombinant IL-1β; (3) iron (delivered as ferrotransferrin, 10 mM Fe$_2$Tf, and chelated with 10 mM–100 mM desferrioxamine (Van Nostrand, et al., *Proc. Natl. Acad. Sci. U.S.A.* 88: 10302 (1991)); (4) desferrioxamine; or (5) left untreated as controls (1×10$^5$ cells). Cells from random wells were counted in order to ensure a consistent presence of 1×10$^5$ cells per well at the beginning of each experiment. Astrocytes were preincubated for 15 minutes in methionine-free medium and pulse-labeled with 300 μCi/ml [$^{35}$S]-methionine for 30 minutes in methionine-free medium (RPMI 1640; GIBCO). Each microtiter plate was washed twice in cold phosphate buffered saline (PBS) at 4° C. before lysis of astrocytes with 25 ml STEN buffer and a sterile glass rod. STEN buffer is 0.2% NP-40, 2 mM EDTA, 50 mM Tris, pH 7.6. The addition of 20 mM PMSF, 5 mg/ml leupeptin to the lysis buffer prevented proteolysis. The buffers from each well were pooled into a total volume of 300 microliters. One half of each pooled lysate was immunoprecipitated with antiserum raised against the carboxyl terminus of APP (1:500 dilution of C-8 antibody raised against amino acid residues 676–695 of APP-695). The remaining portion of each lysate was immunoprecipitated with human ferritin antiserum (1:500 dilution, Boehringer, Indianapolis, Ind.).

Secretion and labeling of APP(s) (protease-nexin-2) from primary astrocytes by IL-1 was measured in a separate set of experiments. Medium from 100 mm dishes (10 ml) of astrocyte cultures was collected after a 2-hour pulse labeling with 200 μCi/ml [$^{35}$S]-methionine. APP in 5 ml of pre-cleared medium was immunoprecipitated using a 1:1500 dilution of rabbit polyclonal serum specific for amino acids 595–611 of APP (R1736, D. Selko). Apolipoprotein E was immunoprecipitated from 5 ml of culture supernatant using a 1:200 dilution of a polyclonal antiserum (Chemicon).

Preparation of Astrocytoma Cells

Astrocytoma cells (60% confluent) were stimulated with IL-1 at the same concentrations as used for primary astrocytes. After stimulation, equal numbers of cells were labeled with 100 μCi/ml [$^{35}$S]-methionine in DMEM medium lacking methionine, washed twice with PBS, and the cell pellets lysed in 200 μl cold STEN buffer containing 20 mM PMSF. APP was immunoprecipitated by adding 2 μl of anti-APP antibody (C-8).

Immunoprecipitations

In all labeling experiments, immunoprecipitated protein was collected by the binding of antibody-labeled antigen complexes to Protein A Sepharose™ beads. Immunoprecipitated samples were applied to 10–20% tris-tricine gels (Novex) and the samples were electrophoresed in tris-tricine buffer according to the manufacturer's instructions. The gels were fixed with 25% methanol, 7% (v/v) methanol for 1 hour, treated with fluorographic reagent (Amplify, Amersham) for 30 minutes, dried, and exposed to X-omat Kodak film overnight at −80° C.

Northern Hybridizations

Total RNA (10 μg) was extracted from primary astrocytes and astrocytoma cells with a RNA-STAT kit (Tel-Test). RNA samples were denatured in 50% formamide/2.2 M formaldehyde/20 mM MOPS/5 mM sodium acetate/0.5 mM EDTA, pH 7.4, at 60° C. for 10 minutes, electrophoresed on 1.0% agarose-formaldehyde gels, blotted onto Hybond-N filters and immobilized by UV crosslinking and heating filters to 80° C. Filters were prehybridized for 3 hours and hybridized overnight in a solution consisting of 50% formamide, 50 mg/ml denatured salmon sperm DNA, 5×SSC, 0.1% sodium dodecyl sulfate and 5×Denhardt's solution. Following hybridization, filters were washed twice for a total of 1 hour in 2×SSC/0.2% sodium dodecyl sulfate at room temperature and twice each for a total of 1 hour in 0.5×SSC/0.1% sodium dodecyl sulfate at 55° C. Equal loading was verified by ethidium bromide staining, non-specific hybridization of the ACT probe to the 28S rRNA, and by standardized hybridization to the GAPDH cDNA probe as an internal standard. The APP cDNA probe corresponded to the unique internal 1 kb fragment gel purified from the 3 kb APP cDNA (Kang et al. *Nature* 325:733 (1987)), the ACT cRNA probe to a PstI/SacI fragment (536–943) in the human ACT cDNA (Chandra, et al, *Biochemistry* 22: 5055 (1983)) and the GAPDH probe to the human GAPDH gene (Tokunaga, et al., *Cancer Res.* 47: 5616 (1987)).

Construction of pSV$_2$(APP)CAT

The pSV$_2$(APP)CAT construct contains the APP gene 5' UTR in between the SmaI and the NruI sites (+52nt and +142nt from the 5' cap site respectively). pSV$_2$(APP)CAT was prepared by two steps of subcloning. (1) A 3 kb SmaI-HindIII fragment containing the APP gene, including the coding region and a segment of the 3' UTR was subcloned into compatible StuI-HindIII sites unique to the 5' UTR of the CAT gene in the pSV$_2$CAT expression vector. (2) The APP gene fragment in between the NruI and HindIII sites was removed from the construct. The restriction sites were then blunt-ended and religated. In the pSV$_2$(APP)CAT transfectants, 90 nt of the APP gene 5' UTR were expressed as part of a chimeric 1171 nt 5' leader in the 1.5 kb APP/CAT transcript. The pSV$_2$CAT construct contains the 5' end of the CAT gene inserted into the unique polylinker site in pBluescript. A 250 nt HindIII/EcoRI fragment from the CAT gene in pSV$_2$CAT was subcloned into the pBS vector (Stratagene). The CAT gene fragment codes for 36 nt of the CAT gene 5' UTR and 218 bp of the 5' end of the coding sequence of the CAT gene.

Transfections

Astrocytoma and neuroblastoma cells were transfected with pSV$_2$CAT or pSV$_2$(APP)CAT by lipofection. Briefly, lipofectamine reagent (Boehringer) was added to DMEM (without serum) and allowed to sit 30 minutes at room temperature. Plasmids (10 μg) in an equal volume of DMEM were then added, and, after sitting for 45 minutes at room temperature, the lipid/DNA solution was added to 60% confluent cells on 100×20 mm cell culture plates. After 4 hours, this solution was removed, and the cells were washed twice in DMEM (without serum). Fresh DMEM medium (containing 10% fetal calf serum) was added. At this time, treatments were administered which included: (1) 0.5 ng/ml IL-1α; (2) 0.5 ng/ml IL-1β; (3) 5 μM Fe$_2$TF (holotransferrin); and (4) unstimulated controls. After 20 hours, cells were harvested in phosphate buffered saline (PBS) and immediately assayed for CAT activity or mRNA levels (RNase protection).

CAT Activity

After harvesting, cells were resuspended in 100 μl 0.25 M Tris, pH 7.8, and subjected to three cycles of freezing (liquid nitrogen) and drying (37° C.) to lyse cells. Lysates were collected after centrifugation at 10,000 rpm for 5 minutes. Protein concentration was determined by a Biorad assay, and exactly 20 μg of lysate was added to a CAT reaction mix containing 50 μl 1M Tris, pH 7.8, 20 μl acetylcoenzyme-A (3.5 mg/ml) and 5 ml $^{14}$C-labeled chloramphenicol (25 mCi/ml). After 1 hour at 37° C., reaction products were extracted with 1 ml ethyl acetate and the samples were resolved by thin layer chromatography as described previously (Rogers, *Blood* 87:2525 (1996)). For quantitative analysis, the areas on the TLC plates which aligned with dots on the film were excised and the radioactivity was counted in 5 ml of scintillation cocktail (Econofluor) using a scintillation counter (Hewlett Packard). In some experiments, CAT activity was measured by counting the amount of CAT reaction product diffusing into liquid scintillation fluid as described previously (Rogers, et al., *Nucl. Acid Res.* 22:2678 (1994)). Each lysate was incubated at 37° C. with [$^3$H]-acetylcoenzyme-A (0.1 mCi) and 20 mM chloramphenicol (CAP) in 200 ml of 100 mm TrisCl (pH 7.8). This aqueous reaction mix had been overlaid by 5 mls of liquid scintillant (Econofluor, NEN).

RNase Protection Experiments

Cells were lysed in 2 ml of a buffer containing 4 M guanidinium thiocyanate, 25 mM NaOac, pH 6.0, 100 mm β-mercaptoethanol. RNA was prepared after shearing the DNA and centrifuging the lysate at 31K, 23° C. for 12 hours through 5 ml of 5.7 M CsCl$_2$ cushion. This procedure ensured that CAT mRNAs and endogenous ferritin mRNAs were purified as a pellet without contamination from plasmid DNA containing transfected CAT gene sequences. The RNA pellet was resuspended in TES buffer (10 mM Tris, pH 7.6, 1 mM EDTA, 0.5% SDS) and was extracted with an equal volume of phenol/chloroform, ethanol-precipitated and resuspended in TES buffer.

Steady-state levels of transfected CAT mRNA from astrocytoma and neuroblastoma pSV$_2$(APP)(CAT) transfectants was characterized by RNase protection. A 261 nucleotide $^{32}$P-labeled cRNA was transcribed from a HindIII digested DNA template isolated from the CAT gene in the pSV$_2$CAT subclone (Rogers, et al., *Nucl. Acid Res.* 22: 2678 (1994); Campbell, et al., *Biochem. Biophys. Res. Commun.* 160: 453 (1989); Fahmy, et al., *Biochem. J.* 296; 175 (1993)). Labeled cRNA, antisense to the CAT gene, was hybridized to 20 μg of mRNA purified from pSV$_2$(APP)(CAT) transfectants of astrocytoma cells. Hybridization was for 24 hours at 45° C. in a buffer containing 80% formamide, 40 mM Pipes (pH 6.7), 0.4 M NaCl, 1 mM EDTA. Digestion with RNase A (40 mg/ml) and RNase T1 (2 mg/ml) removed unhybridized cRNAs. Protected cRNAs were separated by electrophoresis through a 6% polyacrylamide/urea sequencing gel. Kinase labeled HaeIII-digested X-174 DNA fragments were used as DNA markers for autoradiography and quantitation of CAT mRNA levels.

II. Results and Discussion

APP protein synthesis was measured in primary human fetal astrocytes following treatment with 0.5 ng/ml of IL-1α or IL-1β for 16 hours. Experiments were performed in which a 30 minute metabolic labeling with [$^{35}$S]-methionine was followed by APP immunoprecipitation and gel electrophoresis. These indicated that there was a 4-fold increase in the synthesis of intracellular APP in response to IL-1α and a 3-fold increase in response to IL-1β. There was also a 4-fold and a significant 25% up regulation in H-ferritin and L-ferritin subunit synthesis respectively. These experiments show that the APP gene is regulated by IL-1 at the translational level.

IL-1 also induced secretion of APP (APPs; protease-nexin II) from primary human astrocytes. Medium was collected after a 2 hour pulse labeling with [$^{35}$S]-methionine, immunoprecipitated using a N-terminal directed antibody raised against amino acids 595–611 of APP (Sekoe, et al., *Proc. Nat'l Acad. Sci. USA* 85:7341 (1988)) and analyzed by gel electrophoresis and autoradiography. Quantitation of the immunoprecipitate showed a 1.8-fold enhanced secretion of APP(s) into the medium induced by IL-1β and a smaller, 50%, increased accumulation of APP(s) in response to IL-1β. Thus, the levels of both cell-associated and secreted APP were increased by exposure of primary astrocytes to IL-1. The synthesis of the 36 kDa Apo-E protein was measured as an internal standard of IL-1 stimulation and metabolic labeling with [$^{35}$S]-methionine. In both cases no increase in ApoE protein synthesis was observed.

In contract to the IL-1α induced APP protein synthesis in primary astrocytes, there was no observable increase in APP-mRNA levels in measurements by Northern blot analysis indicating that the effect of IL-1 on APP synthesis was at the level of translation. As a control, IL-1α was found to stimulate a pronounced increase in the steady state mRNA levels of alpha-1 antichymotrypsin (ACT) in pure human astrocytes, as has previously been reported (Das, et al., Neuron 14:447 (1995)). Densitometry showed that IL-1α exposure left APP-mRNA levels unchanged while inducing a greater than 10-fold increase in ACT-mRNA levels. Primary astrocytoma cells were grown from a separate fetal brain cortex sample source and, in this confirmatory experiment, GAPDH mRNA levels were used to standardize for loading differences between lanes.

In order to extend the findings with primary human fetal brain astrocytes, the effect of both IL-1α and IL-1β in human astrocytoma (U373MG) cells was tested. Cells were grown to 80% confluence, and equal numbers of cells were stimulated with IL-1α (0.5 ng/ml), IL-1β (0.5 ng/ml) or left unstimulated for 16 hrs. IL-1β as well as IL-1β increased the rate of APP synthesis (maximal 2.8 fold and 4.3 fold respectively) and enhanced the rate of ferritin-H subunit synthesis by 5-fold and L-ferritin by 2 fold in astrocytoma cells. While IL-1α is a more active inducer than IL-1β of APP in primary astrocytes the reverse is true in astrocytoma cells.

As was found for primary astrocytes, IL-1α stimulation of APP gene expression in astrocytoma cells was at the level of translation. In four separate Northern blot experiments, IL-1β stimulated only an average 30% increase in the steady-state levels of APP-mRNAs as standardized to GAPDH-mRNA expression, whereas the cytokine increased APP protein synthesis by 4.3-fold during the same experiment. At the same time, IL-1α and IL-1β each stimulated a large transcriptional increase of ACT mRNA observed in primary human astrocytes. In Northern blots measuring the steady state levels of APP-mRNA and ACT mRNA after 16 hours of IL-1 stimulation, it was found that ACT-mRNA levels in unstimulated cells were undetectable. Low ACT-mRNA expression in unstimulated cells was detected after 48 hours exposure of the blots and allowed for quantitation of a 6-fold induction in steady-state levels of ACT-mRNA.

The translational enhancer region of the L-ferritin gene 5'UTR shows significant sequence alignment with the APP-mRNA 5' leader. A 51% sequence alignment between the L-ferritin and APP-mRNA 5' UTRs was confirmed by computer searching of the APP mRNA (Gap program, GDGDefs software from Univ. of Wisconsin, Madison, Wis.). For this reason, the APP mRNA 5' UTR was considered to be an excellent candidate to carry sequences capable of IL-1-dependent translation enhancement. Previously, the 5' untranslated regions of the L-ferritin and H-ferritin genes (+74 to +142 from the L gene cap site and +139 to +199 from the H-gene cap site) had been shown to confer both baseline and IL-1β dependent translation to a chloramphenicol acetyltransferase (CAT) reporter gene transfected in human hepatoma cells (Rogers, et al., Nucl. Acid Res. 22:2678 (1994); Campbell, et al., Biochem. Biophys, Res. Commun. 160:453 (1989); Fahmy, et al., Biochem. J. 296:175 (1993); Rogers, Blood 87:2525 (1996)). Therefore a pSV$_2$(APP) CAT reporter construct was prepared in which sequences from positions at +55 to +144 nt of the 146 nt APP mRNA 5' UTR were inserted immediately upstream of a hybrid CAT reporter mRNA start codon.

The APP mRNA 5' UTR conferred IL-1 dependent translational enhancement to CAT reporter mRNAs in pSV$_2$ (APP)CAT-transfected astrocytoma cells. The APP mRNA 5' UTR mediated a maximal 3-fold and 4-fold increase in CAT activity following stimulation with IL-1α and IL-1β respectively. IL-1β stimulation of astrocytoma cells transfected with the parental vector pSV$_2$CAT had no effect on CAT activity. These results confirmed that the parental pSV$_2$CAT vector is unresponsive to IL-1 and that the APP-mRNA 5' UTR is important for mediating translational regulation by IL-1 in astrocytoma cells. In a parallel transfection, the IL-1β stimulus caused a 3-fold enhancement of CAT activity in pSV$_2$(APP)CAT transfectants.

The increased CAT activity in the pSV$_2$(APP)CAT-transfected astrocytoma cells following stimulation with either IL-1α or IL-1β was not accompanied by any major changes in APP/CAT mRNA transcription. RNAse protection analysis demonstrated that the steady-state APP/CAT mRNA level was modestly increased (30%) in pSV$_2$(APP) CAT transfected astrocytoma cells relative to unstimulated cells after 16 hours of IL-1β stimulation. Densitometric evaluation of two separate transfections showed that 16 hours of IL-1α stimulation decreased the steady-state level of CAT mRNA by 50% in pSV$_2$(APP)CAT transfectants, while matching experiments evidenced an average 2.3-fold (maximal 4-fold) increase in CAT activity. In addition to mediating IL-1dependent translation, the APP 5' UTR conferred a consistent 6-fold increase in basal CAT activity in pSV$_2$(APP)CAT transfectants compared to the parental astrocytoma cells transfected with pSV$_2$CAT. In this experiment transfections were standardized with the RSV$_2$GAL plasmid, and the amount of CAT gene expression was calculated after transfection efficiencies were taken into account. It was concluded that the APP mRNA 5' UTR acute box sequences enhance IL-1-stimulated translation of APP and also increase baseline activity. This explains the consistent differences in baseline CAT gene expression resulting from pSV$_2$(APP)CAT transfection compared to transfection with pSV$_2$CAT. A similar increase in baseline CAT gene expression has been found after transfection of the light and heavy ferritin mRNA acute boxes into hepatoma cells (Rogers, Blood 87:2525 (1996)).

The data show that IL-1 induces APP protein synthesis by a mechanism of enhanced message translation in two different cellular systems, both of astrocytic origin. This is the second example of translational regulation by IL-1. This cytokine was previously shown to regulate hepatic ferritin translation which may account for part of the anemia of chronic diseases. The most straightforward interpretation of the results is that the primary inflammatory cytokine, IL-1 elevates APP-mRNA translation through the action of an IL-1 responsive stem-loop upstream of the APP gene coding region.

One previous report directly indicates that APP gene expression may be controlled at the level of message translation. APP-mRNA was shown to be expressed as two major forms of mRNA in the human brain resulting from polyadenylation of two poly(A) selection sites (PA-1 and PA-2). The longer APP mRNA (3.3 kB) was found to be translated 3-fold more efficiently than the shorter 3 kB APP mRNA (Sauvage, et al., EMBO J 11:3099 (1992). There are also two studies indirectly suggesting translational regulation of APP protein synthesis. Steady-state levels of APP in the rat cerebral cortex, meninges, and in primary astroglial, microglial, and neuronal cultures do not reflect APP-mRNA levels (LeBlanc, et al., *FEBS Letts.* 292:171 (1991)). Furthermore, the relative levels of APP-695 (KPI–) and APP-751 (KPI+) mRNA and their protein were discordant in human brain. Each message is approximately equally abundant whereas KPI+ proteins are the predominant (>82%) (Van Nostrand, et al., *Proc. Natl. Acad. Sci. U.S.A.* 88:10302 (1991)).

There are striking overlaps in the regulation of the ferritin and APP genes. APP and ferritin are both acute phase reactants (APRs) regulated at the translational level in hepatoma cells (Rogers, et al., *J. Biol. Chem.* 265:14572 (1990)) and primary astrocytes by IL-1. The APP mRNA 5' leader is organized into two regulatory sequences—an iron responsive element (IRE) at the 5' cap site which is responsive to iron, oxidative stress (Pantopolous, et al., *EMBO J.* 14:2917 (1995)) and thyroid hormone receptor (Leedman, et al., *J. Biol. Chem.* 271:12017 (1996)) and a downstream acute box sequence which is both a baseline and IL-1 dependent translation regulatory element that works in an iron dependent fashion. The 5' UTR of the APP gene has an effective acute box sequence in front of the start codon.

However, the APP mRNA 5' leader contains an overlapping sequence upstream of the acute box which is related to the iron responsive element in ferritin mRNA (Klausner, et al., *Proc. Natl. Acad. Sci. USA* 93:8175 (1996)).

IL-1 enhancement of ferritin mRNA translation in hepatic cells and APP protein synthesis in astrocytes suggests that the accumulation of Aβ peptides into plaques during Alzheimer's disease (AD) may be accelerated by a pattern of local protein synthesis in glial cells, similar to a hepatic-style acute phase response. This model of elevated local APP protein synthesis by a cytokine-mediated mechanism is consistent with increasing experimental and epidemiological evidence linking Alzheimer's disease pathology to inflammatory mechanisms. Epidemiological studies show that non-steroidal anti-inflammatory drugs reduce the risk for developing Alzheimer's disease (Andersen, et al., *Neurology* 45:51 (1995)). The over-expression of interleukin-1 by centrally located microglia has been shown to be associated with early forms of amyloid plaques, the non-neuritic diffuse plaques, as well as being strikingly increased during plaque development (Das, et al., *Neuron* 14:447 (1995)). Thus, IL-1 has been suggested as a driving force for amyloid plaque maturation mediated by signaling of the cytokine to astrocytes surrounding the plaque structures and subsequent induction of APP and ACT protein synthesis (Hentz, et al., *Proc. Nat'l Acad. Sci. USA* 93:8175 (1996)). Recently IL-1 injection into the parenchyma of rat cerebral cortex was shown to increase the steady-state level of APP-protein at the site of lesion (Sheng, et al., *Neurobiol. Aging* 17:761 (1996)). The results herein reinforce the view that IL-1 affects APP protein synthesis is increasing APP-mRNA translation.

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

---

---

What is claimed is:

1. A substantially pure DNA molecule comprising:
   a) a translation enhancer element consisting essentially of the nucleotide sequence of SEQ ID NO:1;
   b) a non-homologous gene operably linked to said translation enhancer element.

2. The DNA of claim 1, wherein said non-homologous gene begins at a site between 10 and 100 nucleotides 3' to the last 3' nucleotide in said translation enhancer element.

3. A vector for recombinantly expressing a peptide or protein in a eukaryotic cell comprising:
   a) a promoter which is active in said eukaryotic cell;
   b) a translation enhancer element consisting of the nucleotide sequence of SEQ ID NO:1, wherein said element is 3' to said promoter;

c) a DNA sequence encoding said peptide or protein wherein said DNA sequence:
  i) lies 3' to said translation enhancer element;
  ii) is operably linked to said promoter; and
  iii) is non-homologous to said translation enhancer element.

4. The vector of claim 3, wherein said DNA sequence encoding said peptide or protein begins at a site between 10 and 100 nucleotides 3' to the last 3' nucleotide in said translation enhancer element.

5. A host cell transformed with the vector of claim 3.

6. A host cell transformed with the vector of claim 4.

7. A method for recombinantly producing a peptide or protein comprising:
  a) growing host cells transformed with the vector of claim 3;
  b) purifying said recombinant peptide or protein from either said host cells or from the medium surrounding said host cells.

8. The method of claim 7, wherein the non-homologous gene on said vector begins at a site between 10 and 100 nucleotides 3' to the last 3' nucleotide in said translation enhancer element.

9. The method of claim 7, further comprising contacting said transformed host cells with an inducer in an amount sufficient to significantly increase protein production, wherein said inducer is a cytokine.

10. The method of claim 9, wherein said cytokine is either interleukin-1α; or interleukin-1β.

* * * * *

UNITED STATES PATENT AND TRADEMARK OFFICE
CERTIFICATE OF CORRECTION

PATENT NO. : 6,310,197 B1
APPLICATION NO. : 09/188118
DATED : October 30, 2001
INVENTOR(S) : Jack Rogers It is certified that error appears in the above-identified patent and that said Letters Patent is hereby corrected as shown below:

In column 1, lines 12-14, of the issued patent, the paragraph after "Statement of Government Support" should be corrected to specify the source of funding. The corrected paragraph should read as follows:

-- This invention was made with Government support under Grant No. AI032717 awarded by the National Institutes of Health. The U.S. Government therefore has certain rights in the invention. --

Signed and Sealed this

Eighteenth Day of August, 2009

David J. Kappos
*Director of the United States Patent and Trademark Office*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
GGGAGACGGC GGCGGTGGCG GCGCGGGCAG AGCAAGGACG CGGCGGATCC CACTCGCACA       60

GCAGCGCACT CGGTGCCCCG CGCAGGGTCG                                        90
```